(12) United States Patent
Chen

(10) Patent No.: US 10,946,246 B2
(45) Date of Patent: Mar. 16, 2021

(54) INTERACTIVE MOTION MANAGEMENT DEVICE COMBINED WITH HUMAN PHYSIOLOGICAL INFORMATION AND SPORTS INFORMATION

(71) Applicant: Ya-Chi Chen, New Taipei (TW)

(72) Inventor: Ya-Chi Chen, New Taipei (TW)

(*) Notice: Subject to any disclaimer, the term of this patent is extended or adjusted under 35 U.S.C. 154(b) by 0 days.

(21) Appl. No.: 16/525,156

(22) Filed: Jul. 29, 2019

(65) Prior Publication Data
US 2021/0031072 A1    Feb. 4, 2021

(51) Int. Cl.
*A63B 24/00* (2006.01)
*G08B 5/36* (2006.01)
*G08B 3/10* (2006.01)
*H04Q 9/00* (2006.01)
*A63B 71/06* (2006.01)
*G08B 21/02* (2006.01)

(52) U.S. Cl.
CPC ...... *A63B 24/0062* (2013.01); *A63B 24/0087* (2013.01); *A63B 71/0622* (2013.01); *G08B 3/10* (2013.01); *G08B 5/36* (2013.01); *G08B 21/02* (2013.01); *H04Q 9/00* (2013.01); *A63B 2071/0627* (2013.01); *A63B 2220/836* (2013.01); *A63B 2225/52* (2013.01); *A63B 2225/54* (2013.01); *A63B 2230/06* (2013.01); *A63B 2230/42* (2013.01); *A63B 2230/50* (2013.01); *H04Q 2209/40* (2013.01); *H04Q 2209/823* (2013.01)

(58) Field of Classification Search
CPC .................................................. A63B 24/0062
See application file for complete search history.

(56) References Cited

U.S. PATENT DOCUMENTS

| | | | |
|---|---|---|---|
| 6,744,375 B1 * | 6/2004 | Groos ..................... | A63C 17/22 340/870.07 |
| 7,938,752 B1 * | 5/2011 | Wang ................. | A63B 24/0087 482/4 |
| 9,308,417 B2 * | 4/2016 | Grundy ............. | A63B 21/0726 |
| 2009/0029754 A1 * | 1/2009 | Slocum ............. | A63B 71/0622 463/5 |
| 2019/0192912 A1 * | 6/2019 | Hwang ............. | A63B 24/0006 |
| 2020/0101343 A1 * | 4/2020 | Gonzales ................. | A63B 5/16 |
| 2020/0184846 A1 * | 6/2020 | Zhang ................ | G09B 19/0038 |

* cited by examiner

*Primary Examiner* — Qutbuddin Ghulamali

(57) ABSTRACT

An interactive sports management device combined with human physiological information and sports information includes a user module, an exercise module and a management module, wherein the user module is used to detect the physiological information of the user, and transmit the user identifier and the physiological information to the exerciser module. The exercise module is used to collect the sports information of the sports fitness equipment, and transmit the user identifier, the physiological information, the exerciser identifier and the sports information to the management module. The management module transmits the management information to the exerciser module. In this way, the sports information generated when the specific person uses the specific sports fitness equipment for exercise is combined with the human physiological information into the personalized information.

14 Claims, 6 Drawing Sheets

INTERACTIVE MOTION MANAGEMENT DEVICE COMBINED WITH HUMAN PHYSIOLOGICAL INFORMATION AND SPORTS INFORMATION

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present invention relates generally to the sports fitness field, and more particularly to an interactive sports management device combined with human physiological information and sports information.

2. Description of Related Art Including Information Disclosed Under 37 CFR 1.97 and 37 CFR 1.98

Appropriate exercise is conducive to promoting physical health and releasing stress. Limited by working hours, weather or field and other environmental conditions, in recent years, the lifestyle of sports in a gymnasium setting has been gradually developed. Under the guidance of professional coaches, one can use the different types of sports equipment in gymnasium for different forms of exercise based on personal needs.

Existing sports equipment can detect and record the use course information, provide users or coaches with access, also it can be seen that there is a personal wearable sport sensor for sensing and recording personal physiological information such as heartbeat in exercising, providing users with reference of whether the goal of sports is achieved.

However, this structural type has been found that the following problems still exist in practical application experience: the gym is provided with a variety of sports equipment, each sports equipment is usually several or even dozens, and there are multiple users to use the multiple identical or different sports equipment for exercising in the gym, and individual user also often use multiple different sports equipment during the same exercise period, the existing sports equipment is unable to distinguish the use state of specific users, the personal wearable sport sensor cannot distinguish the sport type, which is not conducive to that the user or the coach determines whether have the need to strengthen or change the forms of exercise.

BRIEF SUMMARY OF THE INVENTION

The present invention mainly aims to provide the instructions of using sports fitness equipment combined with human physiological information and sports information, and the technical problem to be solved is how to develop the instructions of the new sports fitness equipment combined with human physiological information and sports information for the innovative breakthrough, which has more ideal practicality.

Based on the foregoing objects, the present invention provides an interactive sports management device combined with human physiological information and sports information, including a user module, an exerciser module and a management module, wherein the user module is disposed in a wearable device of the user, and the exerciser module is disposed in a sports fitness equipment, the user module transmits a information to the exerciser module, and the exerciser module and the management module transmit information to each other;

The user module includes a physiological information collector, a first microcontroller and a first wireless communicator, wherein the physiological information collector and the first wireless communicator are respectively coupled with the first microcontroller, so that the first microcontroller controls respectively the physiological information collector and the first wireless communicator; the physiological information collector is used to sense physiological information of the user, and transmit the physiological information to the first microcontroller, the first microcontroller is provided with a user identifier, the first microcontroller transmits the user identifier and the physiological information to the first wireless communicator, the first wireless communicator is used to transmit outwards the user identifier and the physiological information;

The exerciser module includes a second microcontroller, a second wireless communicator, a sports information collector, a first display, a first operating unit and a second operating unit, wherein the second wireless communicator, the sports information collector, the first display, the first operating and the second operating unit are respectively coupled with the second microcontroller, so that the second microcontroller respectively controls the second wireless communicator, the sports information collector and the first display; the sports information collector is used to collect the sports information of the sports fitness equipment, and transmit the sports information to the second microcontroller. The second microcontroller is provided with an exerciser identifier, and the second wireless communicator is used to receive the user identifier, the physiological information and the management information transmitted by the management module, and transmit the user identifier, the physiological information, the sports information and the exerciser identifier to the management module. The first display is used to display the status of the sports fitness equipment, and the first operating unit is a control loop for sending a control instruction to the second microcontroller, thereby controlling the exercise module to receive the physiological information transmitted by the user module. The second operating unit is a control loop used to send a control instruction to the second microcontroller, thereby controlling the exerciser module to interrupt the physiological information transmitted by the user module;

The management module includes a third microcontroller, a third wireless communicator and a storage, wherein the third microcontroller is coupled with the third wireless communicator and the storage, so that the third microcontroller controls the third wireless communicator, the third wireless communicator is used to receive the user identifier, the physiological information, the sports information and the exercise identifier, and transmit the management information, so that the user or the coach determines whether to adjust the sport item or the strength. The third microcontroller is used to process the user identifier, the physiological information, the sports information and the exerciser identifier; and the user identifier, the physiological information, the sports information and the exerciser identifier are stored in the storage unit.

With this innovative and unique design, the present invention can combine the sports information of a specific sports fitness equipment used by the specific person with the physiological information of the human body into personalized information according to the prior art, as a basis to determine whether it is necessary to strengthen, reduce or change the sports type, so as to satisfy the user's need for specific sports purposes and avoid over-exercise, even if multiple sports fitness equipments are used by multiple people, each user's personalized physiological information and sports information can be clearly distinguished.

Another object of the present invention is to provide an exerciser module for the aforementioned interactive sports management device combined with human physiological information and sports information.

DETAILED DESCRIPTION OF THE INVENTION

The figures illustrate several specific possible embodiments of the present invention, but Embodiments are for illustrative purposes only, which is not subject to this structure in the patent application.

Figure 1:
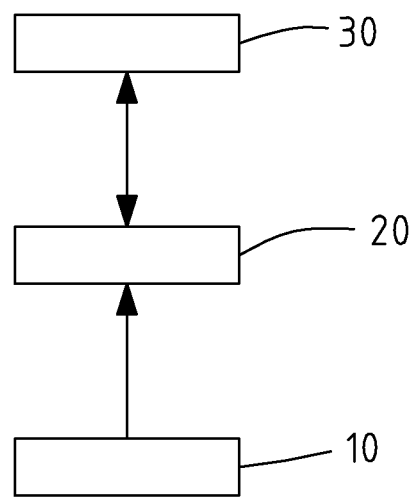
FIG. 1 is an online schematic diagram of Embodiment 1 of the present invention.

As shown in FIG. 1, an embodiment of an interactive sports management device combined with human physiological information and sports information of the present invention includes a user module 10, an exerciser module 20 and a management module 30, wherein the user module 10 may be disposed in the wearable device of the user (not shown in the figure), the wearable device may be a chest strap worn on the chest of the user, a wrist support worn on the wrist, a bind ring worn on the upper arm or other devices that may be disposed on the user' body without adverse effect. The device module 20 is disposed in a sports fitness equipment (not shown in the figure), and the user module 10 transmits an information to the exerciser module 20. The exerciser module 20 and the management module 30 transmit the information to each other.

Figure 2:
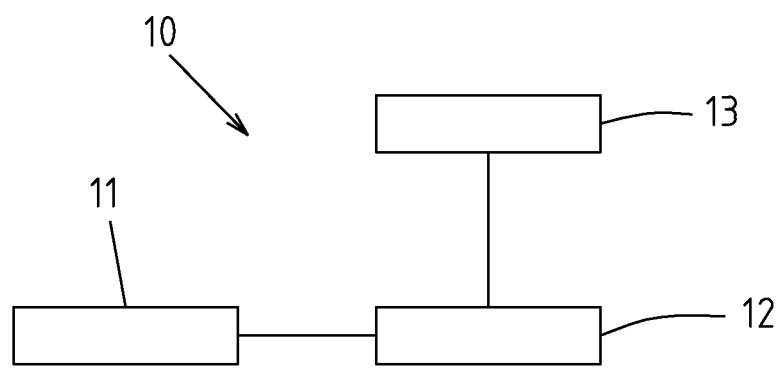
FIG. 2 is a circuit block diagram of a user module of Embodiment 1 of the present invention.

As shown in FIGS. 1 and 2, the user module 10 includes a physiological information collector 11, a first microcontroller 12 and a first wireless communicator 13, wherein the physiological information collector 11 and the first wireless communicator 13 are respectively coupled with the first microcontroller 12, so that the first microcontroller 12 controls respectively the physiological information collector 11 and the first wireless communicator 13. The physiological information collector 11 is used to sense the physiological information of the user, and transmit the physiological information to the first microcontroller 12. The physiological information includes one or several values of a heartbeat frequency value, a respiratory frequency value, and a body temperature, and the physiological information is not only limited to the heartbeat frequency value, a respiratory frequency value and a body temperature listed above. The first microcontroller 12 is a microcontroller (Microcontroller Unit, MCU), and the first microcontroller 12 is provided with a user identifier. The user identifier is used as the basis for the management module 30 to determine that the physiological information is collected by the physiological information collector 11 from a specific user. The first microcontroller 12 transmits the user identifier and the physiological information to the first wireless communicator 13. The first wireless communicator 13 is used to transmit outwards the user identifier and the physiological information.

Figure 3:
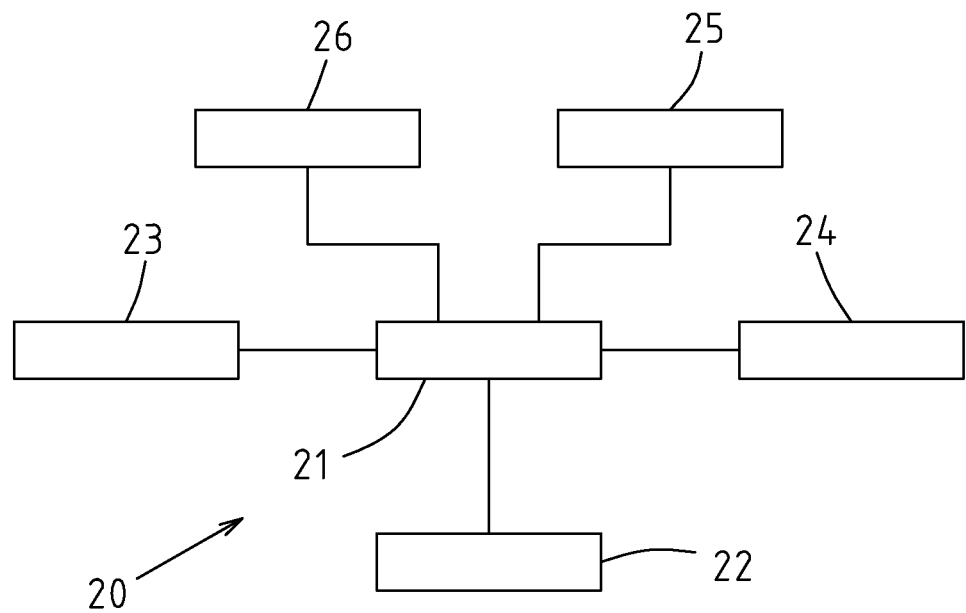
FIG. 3 is a circuit block diagram of an exerciser module of Embodiment 1 of the present invention.

As shown in FIGS. 1 and 3, the exerciser module 20 includes a second microcontroller 21, a second wireless communicator 22, a sports information collector 23, a first display 24, a first operating unit 25 and a second operating unit 26, wherein a second wireless communicator 22, a sports information collector 23, a first display unit 24, a first operating unit 25 and a second operating unit 26 are respectively coupled with the second microcontroller 21, so that the second microcontroller 21 respectively controls the second wireless communicator 22, the sports information collector 23 and the first display 24. The sports information collector 23 is used to collect the sports information of the sports fitness equipment, and transmit the sports information to the second microcontroller 21. The second microcontroller 21 is a microcontroller, and the second microcontroller 21 is provided with an exerciser identifier. The exerciser identifier is used as the basis for the management module 30 to determine that the sports information is collected by the sports information collector 23 from the specific sports fitness equipment. The second wireless communicator 22 is used to receive the user identifier, the physiological information and the management information transmitted by the management module 30, and to transmit the user identifier, the physiological information, the sports information and the exercise identifier to the management module 30. The first display 24 is used to display the status of the sports fitness equipment, the first operating unit 25 is a control loop for providing the user's operation, so that a control instruction is sent to the second microcontroller 21 for controlling the exerciser module 20 to receive the physiological information transmitted by the user module 10. The second operating unit 26 is a control circuit for providing the user's operation, hereby sending a control instruction to the second microcontroller 21 for controlling the operator module 20 execution to interrupt receiving the physiological information transmitted by the user module 10.

Figure 4:
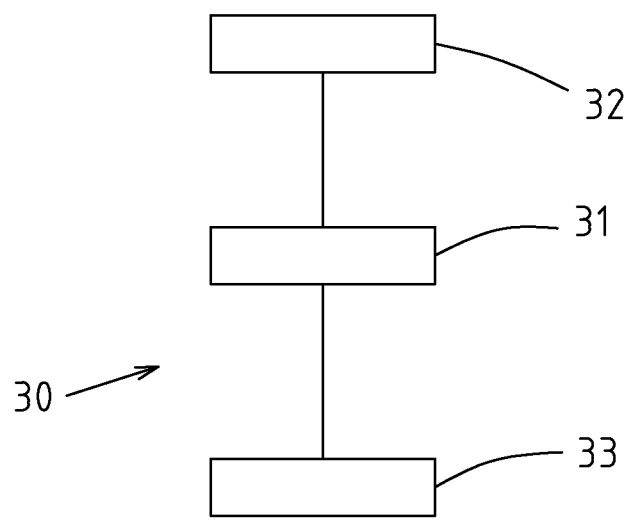
FIG. 4 is a circuit block diagram of a management module of Embodiment 1 of the present invention.
Figure 5:
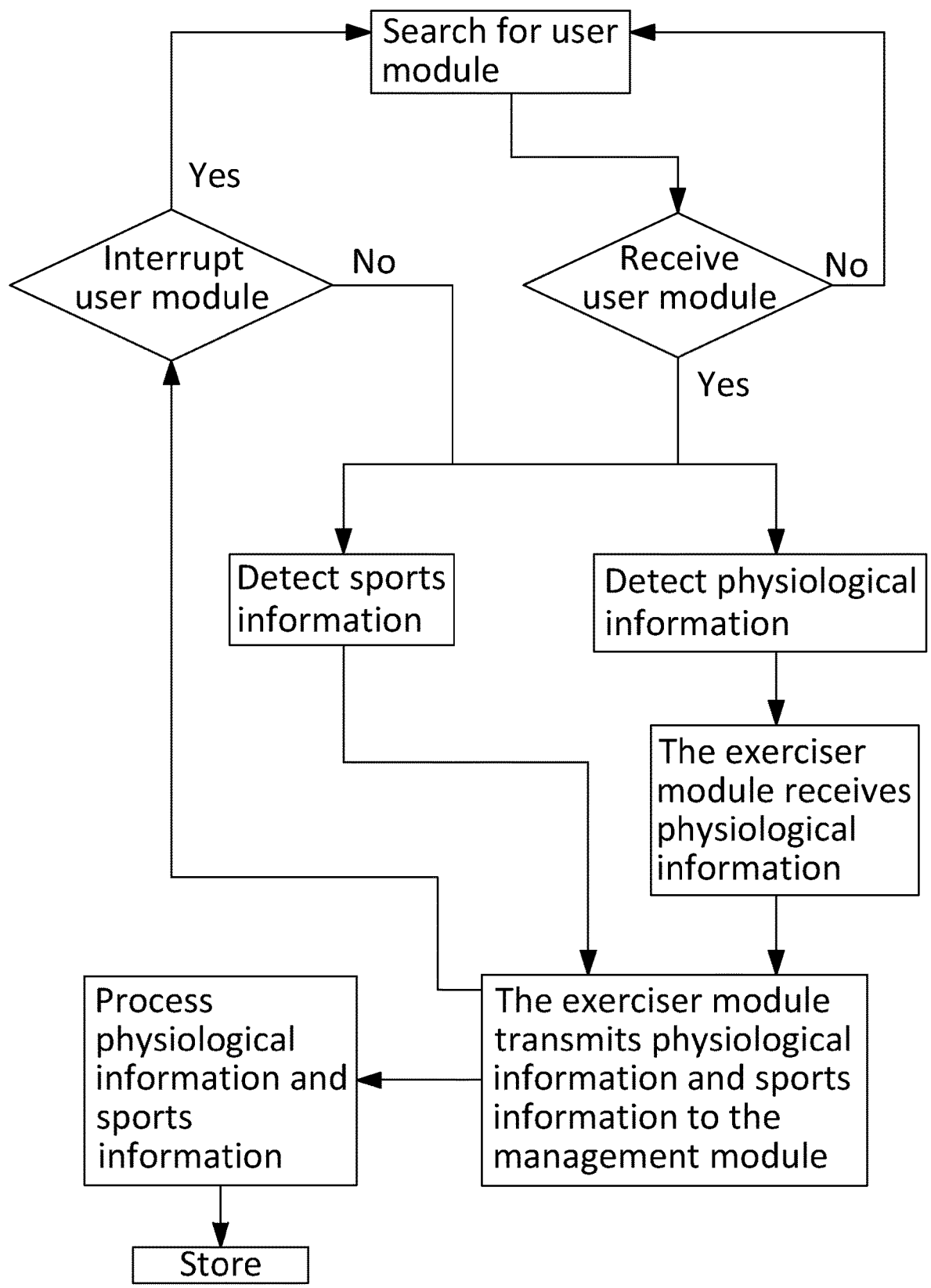
FIG. 5 is a logical block diagram of Embodiment 1 of the present invention.

As shown in FIGS. 1 and 4, the management module 30 includes a third microcontroller 31, a third wireless communicator 32 and a storage 33, wherein the third microcontroller 31 is coupled with the third wireless communicator 32 and the storage 33, so that the third microcontroller 31 controls the third wireless Communicator 32. The third wireless communicator 32 is used to receive the user identifier, the physiological information, the sports information and the executive identifier, and transmit outwards the management information. The third microcontroller 31 is a microcontroller 31 for processing the user identifier. The processed user identifier, the physiological information, the sports information and the exerciser identifier are stored in the storage unit 33.

Based on said structural composition type and technical features, the operation of Embodiment 1 of the present invention is described as follows:

As shown in FIG. 1-FIG. 5, the exercise module 20 searches for whether there is any user module 10 in the environment of the sports fitness equipment based on the user module 10 transmitting the signal including the user identifier and the physiological information through the first wireless communicator 13. The received user identifier is transmitted to the second microcontroller 21, and the second microcontroller 21 controls the first display 24 to display the user identifier. At this time, the second wireless communicator 22 receives one or several signals including the user identifier signal and the user identifiers of the signals are different. The second microcontroller 21 controls the first display 24 correspondingly to display one to several user identifiers according to the signal received by the second wireless communicator 22. The user selects the corresponding user identifier of the user module 10 configured by the self-wearable device, and operates the first operating unit 25, so that the exerciser module 20 receives the physiological information transmitted by the user module 10, and refuses to receive the physiological information transmitted by other user modules, and completes the user module 10 paired with the exerciser module 20.

Based on that exerciser module 20 receives the user identifier and the physiological information transmitted by the user module 10, the sports information collector 23 begins to continuously collect the sports information of the sports fitness equipment and transmits the sports information to the second microcontroller 21. The user can start using the sports fitness equipment to exercise. The user module 10 continuously detects the physiological information of the user and transmits the information to the exerciser module 20. The second microcontroller 21 transmits the physiological information, the user identifier, the sports information and the built-in exerciser identifier of the second microcontroller 21 to the management module 30 through the second wireless communicator 22; at the same time, the second microcontroller 21 can also select to control the first display 24 for synchronously displaying the physiological information and the sports information, and providing the user with real-time changes in the self-physiological state and exercise intensity.

The third wireless communicator 32 of the management module 30 receives the information transmitted by the second wireless controller 22, including the physiological information, the user identifier, the sports information and the exercise identifier, and transmits the information to the third microcontroller 31, the third microcontroller 31 deciphers and processes the information, and stores the physiological information, the sports information and the exerciser identifier in the data block with the same user identifier in the storage 33 according to the user identifier.

According to the foregoing, the present invention can combine the human body information of a specific person with the sports information of the specific person engaged in sports, and provide the information to the specific person and professional coach for viewing at any time, and as a reference for the selection and strength of the future sports fitness program.

It is worth mentioning that in an environment with multiple sports fitness equipment of the same or different types, when multiple people are engaged in sports, the exerciser module 20 can identify a plurality of different user modules 10 through the user identifier. And the physiological information generated by the specific user module 10 and the sports information generated by the exerciser module 20 are transmitted to the management module 30. The management module 30 identifies a plurality of different user modules 10 and a plurality of different exerciser modules 20 through the user identifier and the exerciser identifier, so that the management module 30 can bind the physiological information and the sports information generated by the specific person to use the specific sports fitness equipment. The information stored in the storage 33 after deciphering can be easily personalized in management, and each group of personalized information stored in the storage 33 can show the specific sport item, intensity and time of the specific person, which is beneficial for the user or the coach to determine whether it is necessary to strengthen, reduce the intensity of exercise or change the sport type, satisfy the user's demand for specific sports purposes and avoid injury due to over-exercise.

The management module 30 may actively transmit the physiological information and the sports information to the external device with prior authorization or the cloud by using the third wireless communicator 32 according to the user identifier. The external device may be the mobile communication device used by the user or the mobile communication device used by the coach or the management system of the sports fitness center provided, which are provided to the user or the coach to determine whether it is necessary to further adjust the sport item or intensity.

Further, based on that the exerciser module 20 transmits the physiological information, the user identifier and the sports information to the management module 30, if the user needs to stop using the sports fitness equipment, the user may select to operate the second operating unit 26. At this time, the second operating unit 26 transmits a signal to the second microcontroller 21. After it is read by the second microcontroller 21, it interrupts to receive the physiological information transmitted by the user module 10 and transmits a signal to the sports information collector 23. It stops to collect the sports information, the exerciser module 20 replies to any status of the user module 10, the user can leave the sports fitness equipment, choose to rest or use other sports fitness equipment for exercise.

Further, the first operating unit 25 and the second operating unit 26 can respectively be provided with buttons or knobs or other forms of switches for operation, which is provided to the user for selection and operation, the first operating unit 25 and the second operating unit 26 may also be selected in the first display 24 to display a continuous dynamic change image of a fixed icon or a sliding operation for the user to touch.

Figure 6:
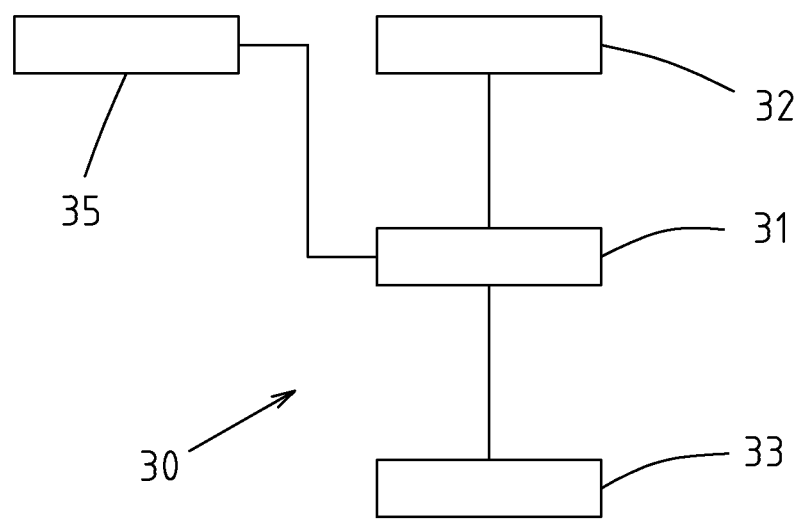
FIG. 6 is a circuit block diagram of a management module of Embodiment 2 of the present invention.

Embodiment 2 is changed from Embodiment 1, and Embodiment 2 is the same composition as Embodiment 1 in the description. As shown in FIG. 6, Embodiment 2 differs from the composition of Embodiment 1 mainly in the composition that the management module 30 further comprises a second display 35 electrically connected with the third microcontroller 31. The second display 35 is used to display the physiological information and sports information; accordingly, the physiological information and the sports information generated by the user using the sports fitness equipment can be displayed on the second display 35 in real time, and provided to the coach to determine whether it is necessary further to adjust the sport item or intensity.

Figure 7:
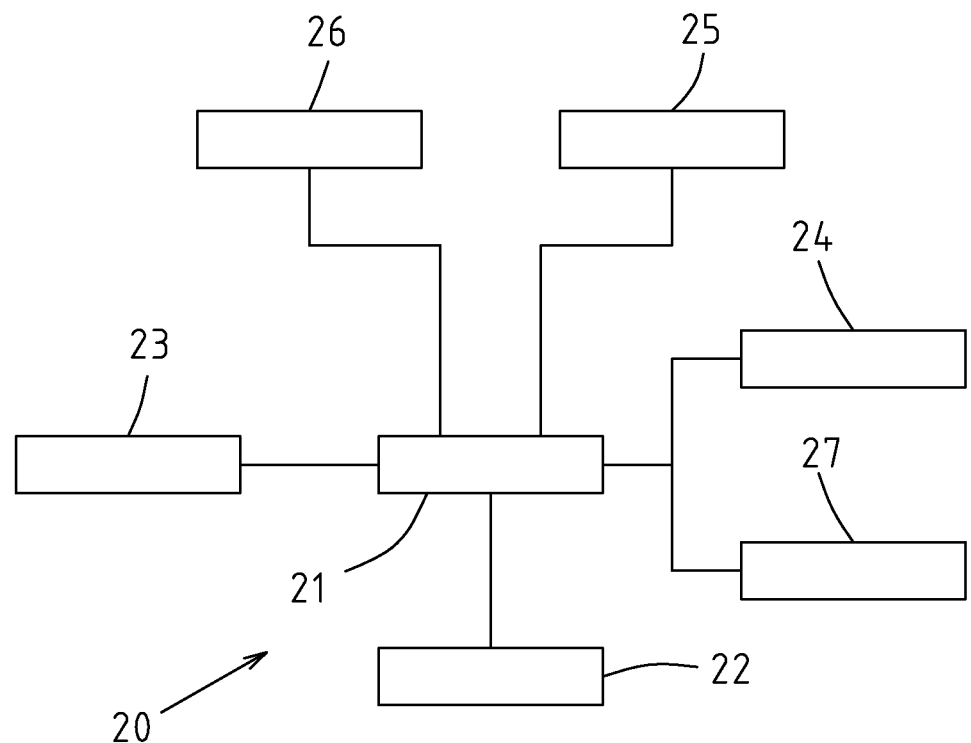
FIG. 7 is a circuit block diagram of an exerciser module of Embodiment 3 of the present invention.

Embodiment 3 is changed from Embodiment 1, and Embodiment 3 is the same composition as Embodiment 1 in the description. As shown in FIG. 7, Embodiment 3 differs from the composition of Embodiment 1 mainly in the composition that the exerciser module 20 further comprises a first warning indicator 27, the first warning indicator 27 is electrically connected with the second microcontroller 21, and the first warning indicator 27 is used to generate a warning message.

Except for that Embodiment 3 can perform the same operation as the foregoing Embodiment 1, and the management module (not shown in the figure) compares the received physiological information with a default warning threshold, when the physiological information is higher or lower than the warning threshold value, the management module transmits a signal to the exerciser module 20, and the second microcontroller 21 controls the first warning indicator 27 to generate a warning message based on the signal, thereby prompting the user to stop the exercise or perform a gradual slow exercise. Other people in the environment can also use the warning message to take timely assistance or rescue measures to reduce the risk of accidents.

The first warning indicator 27 may select one or more of the buzzer, a warning lamp and other instruments capable of emitting a warning sound or warning light, and the exerciser module 20 may also select a first display 24 to display a warning message.

Figure 8:
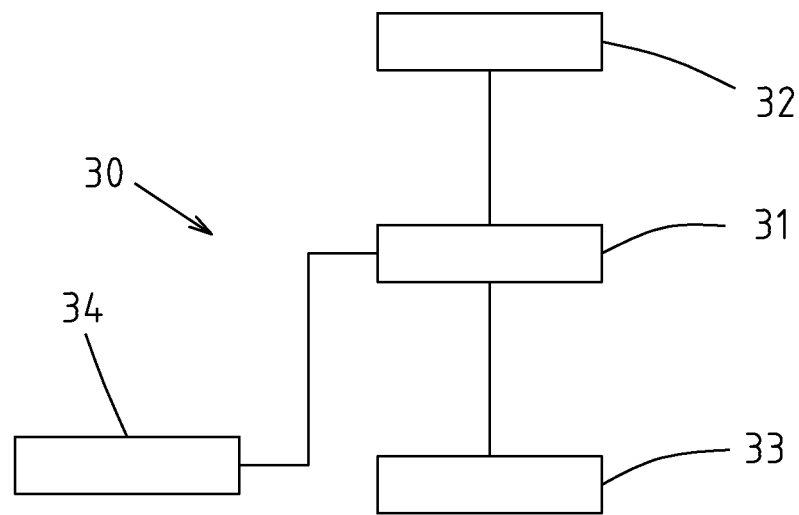
FIG. 8 is a circuit block diagram of a management module of Embodiment 4 of the present invention.

Except for that Embodiment 4 is changed from Embodiment 3, and Embodiment 4 is the same composition as Embodiment 3 in the description. As shown in FIG. 8, Embodiment 4 differs from the composition of Embodiment 3 mainly in that management module 30 further comprises a second warning indicator 34, the second warning indicator 34 is electrically connected with the third microcontroller 31, and the second warning indicator 34 is used to generate a warning message.

Embodiment 4 can perform the same operation as the foregoing Embodiment 3, when the physiological information is higher or lower than the preset warning threshold, the management module 30 transmits the signal to the exerciser module, and the third microcontroller 31 controls the second warning indicator 34 to generate a warning message, thereby prompting the system administrator or the gym administrator or the coach at a remote location, so that they can take corresponding assistance or rescue measures in time to reduce the risk of the accident.

The second warning indicator 34 may select one or more of a buzzer, a warning lamp, and other instruments capable of emitting a warning sound or warning light. Embodiment 4 may also be the same as the foregoing embodiment 2, optionally further including a second display (not shown in the figure), hereby a modified embodiment of Embodiment 4 is composed, and the second display is used to display the warning message.

Figure 9:
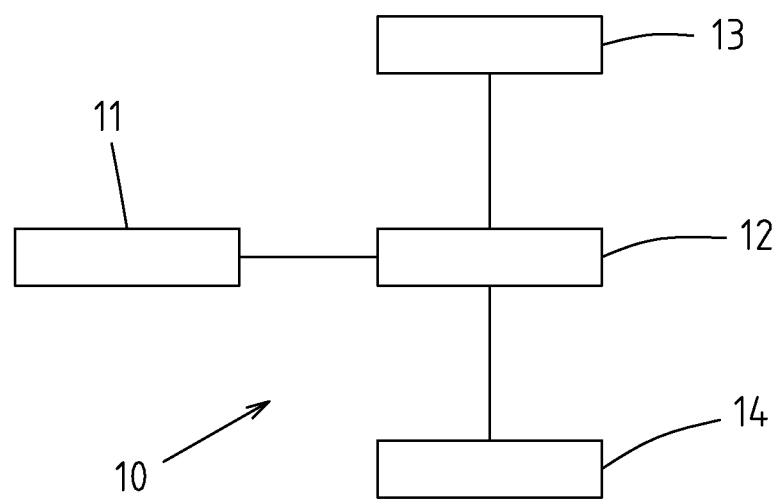
FIG. 9 is a circuit block diagram of a user module of Embodiment 5 of the present invention.

Embodiment 5 is changed from Embodiment 1, and Embodiment 5 is the same composition as Embodiment 1 in the description. As shown in FIG. 9, Embodiment 5 differs from the composition of Embodiment 1 mainly in that the user module 10 further comprises a start switch 14, the start switch 14 is electrically connected with the first microprocessor 12, thereby controlling the operation or stop of the user module 10; when the user wants to use the sports fitness equipment for the fitness exercise, the start switch 14 is operated to start the user module 10, and the user module 10 starts detecting the physiological information of the user, and transmits outwards the user identifier and the physiological information. When the user stops to use the sports fitness equipment, the start switch 14 can be operated to stop the operation of the user module 10, thereby reducing the power consumption and increasing the service life of the user module 10.

Figure 10:
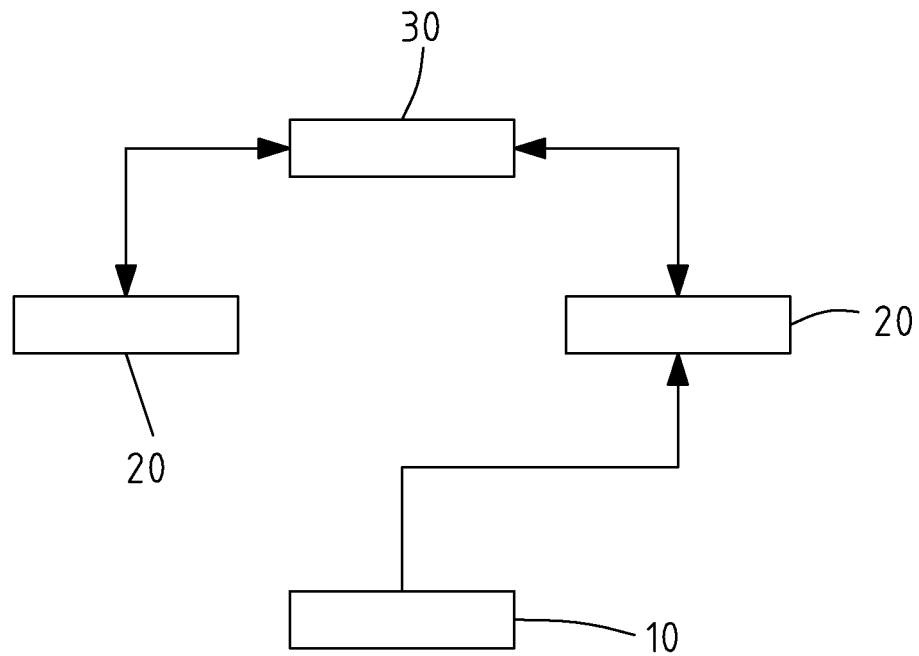
FIG. 10 is an online schematic diagram of Embodiment 6 of the present invention.

Embodiment 6 is changed from Embodiment 1. As shown in FIG. 10, Embodiment 6 includes a user module 10, a plurality of exerciser modules 20 and a management module 30, wherein the user module 10 can be disposed in a wearable device (not shown in the figure), each of the exerciser modules 20 is respectively disposed in a plurality of sports fitness equipment (not shown in the figure). When the user operates any of the exerciser module 20, the user module 10 can selectively transmits a message to any exerciser module 20, and each of the exerciser module 20 and the management module 30 transmit a message to each other; the specific composition of the user module 10, the exerciser module 20 and the management module 30 of Embodiment 6 is the same as the user module 10, the exerciser module 20 and the management module 30 of Embodiment 1, Embodiment 2 or Embodiment 3 or Embodiment 4.

Figure 11:
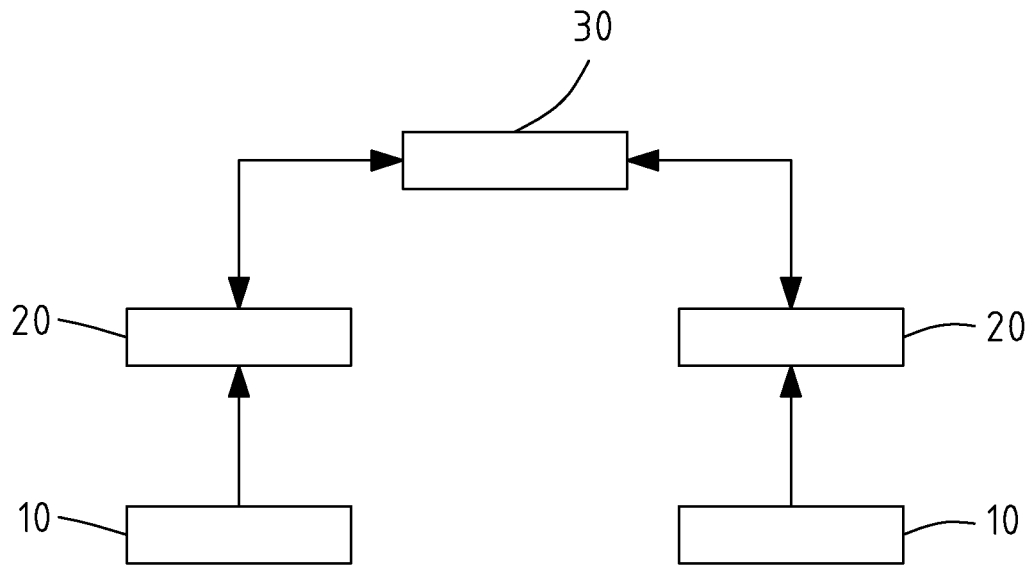
FIG. 11 is an online schematic diagram of Embodiment 7 of the present invention.

Embodiment 7 is changed from Embodiment 1. As shown in FIG. 11, Embodiment 7 includes a plurality of user modules 10, a plurality of exerciser modules 20 and a management module 30, wherein each user modules 10 can be respectively disposed in different wearable devices (not shown in the figure) provided for different users to wear, and each exerciser modules 20 is respectively disposed in several sports fitness equipment (not shown in the figure). When each user respectively selects each exerciser module 20, each user module 10 can selectively transmit information to the different exerciser module 20, each exerciser module 20 and the management module 30 transmit a message to each other; the specific composition of each user module 10, each exerciser module 20 and the management module 30 of Embodiment 7 can be the same as the user module 10, the exerciser module 20 and the management module 30 of Embodiment 1, Embodiment 2 or Embodiment 3 or Embodiment 4.

The present invention can combine the sports information of the specific sports fitness equipment with the physiological information of the human body in exercising, and provide the information to a user or a professional coach for the application as a basis to determine whether it is necessary to strengthen, reduce or change the sport type, satisfy the demand of the user for specific sports purposes, and avoid the injury due to over-exercise, even when multiple sports fitness equipments are used by multiple people, the personalized physiological information and sports information of each user can be clearly distinguished.

I claim:

1. An interactive sports management system that combines human physiological information and sports information, the interactive, sports management system comprising:
   a user module having a physiological information collector and a first microcontroller and a first wireless communicator, wherein the physiological information collector and the first wireless communicator are respectively coupled to the first microcontroller such that the first microcontroller respectively controls the physiological information collector and the first wireless communicator, wherein said user module is disposed in a wearable device adapted to be worn by a user, wherein the physiological information collector senses physiological information of the user and transmits the physiological information and a built-in user identifier to the first microcontroller, the first microcontroller transmits the user identifier and the physiological information to the first wireless communicator, wherein the first wireless communicator transmits the user identifier and the physiological information;

an exercise module having a second microcontroller and a second wireless communicator and a sports information collector and a first display and a first operating unit and a second operating unit, wherein the second wireless communicator and the sports information collector and the first display and the first operating unit and the second operating unit are respectively coupled to the second microcontroller such that the second microcontroller respectively controls the second wireless communicator and the sports information collector and the first display, wherein the sports information collector collects sports information from a fitness equipment and transmits the sports information to the second microcontroller, the second microcontroller having an exercise identifier; and a management module having a third microcontroller and a third wireless communicator and a storage, wherein the third microcontroller is coupled to the third wireless communicator and the storage such that the third microcontroller controls the third wireless communicator, the third wireless communicator receives the user identifier and the physiological information and the sports information and the exercise identifier, wherein the second wireless communicator receives the user identifier and the physiological identifier information and management information transmitted by said management module, the second wireless communicator transmitting the user identifier and the physiological information and the sports information and the exercise identifier to the management module, wherein the first display displays a status of the item of fitness equipment, wherein the first operating unit has a control loop that transmits a control instruction to the second microcontroller so as to control said exercise module in order to receive the physiological information transmitted by said user module, wherein the second operating unit has another control loop that transmits a control instruction to the second microcontroller so as to control said exercise module in order to interrupt receipt of the physiological information transmitted by said user module, wherein the third wireless communicator receives the user identifier and the physiological information and the sports information and the exercise identifier and transmits the management information so as to allow the user to determine whether the item of fitness equipment or a strength should be adjusted, wherein the third microcontroller processes the user identifier and the physiological information and the sports information and the exercise identifier, wherein the user identifier and the physiological information and the sports information and the exercise identifier are stored in the storage.

2. The interactive sports management system of claim 1, wherein said management module has a second display electrically connected to the third microcontroller, the second display of said management module displaying the physiological information and the sports information.

3. The interactive sports management system of claim 2, wherein said exercise module has a first warning indicator to send a warning message when the physiological information is normal.

4. The interactive sports management system of claim 3, wherein the first warning indicator is a buzzer or a warning lamp.

5. The interactive sports management system of claim 3, wherein said management module has a second warning indicator electrically connected to the third microcontroller to send a warning message when the physiological information is abnormal.

6. The interactive sports management system of claim 3, wherein the physiological information is selected from the group consisting of at least one of a heart rate frequency value, a respiratory rate and a body temperature.

7. The interactive sports management system of claim 2, wherein the physiological information is selected from the group consisting of at least one of a heart rate frequency value, a respiratory rate and a body temperature.

8. The interactive sports management system of claim 1, wherein said exercise module has a first warning indicator to send a warning message when the physiological information is normal.

9. The interactive sports management system of claim 8, wherein the first warning indicator is a buzzer or a warning lamp.

10. The interactive sports management system of claim 8, wherein said management module has a second warning indicator electrically connected to the third microcontroller to send a warning message when the physiological information is abnormal.

11. The interactive sports management system of claim 8, wherein the physiological information is selected from the group consisting of at least one of a heart rate frequency value, a respiratory rate and a body temperature.

12. The interactive sports management system of claim 1, wherein the physiological information is selected from the group consisting of at least one of a heart rate frequency value, a respiratory rate and a body temperature.

13. The interactive sports management system of claim 1, wherein said user module has a start switch electrically connected to said first microcontroller to control an operation of said user module or to stop the operation.

14. The interactive sports management system of claim 1, wherein said second microcontroller has a first warning indicator to send a warning message when the physiological information is abnormal.

* * * * *